United States Patent [19]

Sovik et al.

[11] Patent Number: 5,900,736

[45] Date of Patent: May 4, 1999

[54] PAVING MATERIAL DENSITY INDICATOR AND METHOD USING CAPACITANCE

[75] Inventors: Robert A. Sovik, Clifton Park; Richard N. Hosterman, Buskirk; George G. Moross, Scotia, all of N.Y.

[73] Assignee: Transtech Systems, Inc., Schenectady, N.Y.

[21] Appl. No.: 08/901,437

[22] Filed: Jul. 28, 1997

[51] Int. Cl.$^6$ ................................................ G01R 27/26
[52] U.S. Cl. .......................... 324/663; 324/687; 324/690
[58] Field of Search .................................... 324/659, 667, 324/674, 681, 686, 688, 690, 663, 687; 73/73, 74; 404/17, 75, 72

[56] References Cited

U.S. PATENT DOCUMENTS

| | | | |
|---|---|---|---|
| 3,400,331 | 9/1968 | Harris | 324/671 |
| 3,671,857 | 6/1972 | Bergmanis et al. | 324/663 |
| 3,694,742 | 9/1972 | Bergmanis et al. | 324/663 |
| 3,781,672 | 12/1973 | Maltby et al. | 324/663 |
| 3,784,905 | 1/1974 | Blackwell | 324/663 |
| 3,882,381 | 5/1975 | Gregory | 324/667 |
| 3,967,912 | 7/1976 | Parker | 404/84.05 |
| 4,099,118 | 7/1978 | Franklin et al. | 324/671 |
| 4,389,136 | 6/1983 | Fehrenbach | 404/75 |
| 4,433,286 | 2/1984 | Capots et al. | 324/663 |
| 4,468,610 | 8/1984 | Hanson | 324/665 |
| 4,604,612 | 8/1986 | Watkins et al. | 340/582 |
| 4,766,369 | 8/1988 | Weinstein | 324/670 |
| 4,817,021 | 3/1989 | Sowerby et al. | 324/687 |
| 4,933,853 | 6/1990 | Musil et al. | 364/424.07 |
| 4,972,154 | 11/1990 | Bechtel et al. | 324/663 |
| 5,051,026 | 9/1991 | Sovik | 404/118 |
| 5,088,854 | 2/1992 | Sovik | 404/72 |
| 5,134,380 | 7/1992 | Jonas | 324/674 |
| 5,138,268 | 8/1992 | Mulkey et al. | 324/671 |
| 5,210,500 | 5/1993 | Pingel et al. | 324/667 |
| 5,213,442 | 5/1993 | Sovik | 404/102 |
| 5,223,796 | 6/1993 | Waldman et al. | 324/687 |
| 5,309,110 | 5/1994 | O'Neill et al. | 324/674 |
| 5,363,051 | 11/1994 | Jenstrom et al. | 324/661 |
| 5,378,994 | 1/1995 | Novak et al. | 324/671 |
| 5,398,547 | 3/1995 | Gerardi et al. | 324/688 |
| 5,436,565 | 7/1995 | Gammell | 324/690 |
| 5,484,226 | 1/1996 | Emerson et al. | 404/84.05 |
| 5,521,515 | 5/1996 | Campbell | 324/674 |
| 5,551,288 | 9/1996 | Geraldi et al. | 324/671 |
| 5,602,486 | 2/1997 | Novak | 324/663 |

FOREIGN PATENT DOCUMENTS 2 593 200  1/1986  France .

OTHER PUBLICATIONS

Time domain technique for low frequency dielectric measurements/J. Phys. E: Sci. Instrum., vol. 13 (1980); Printed in Great Britian (month unavailable).
Evaluation of Dielectric Measurement Apparatus For Determining Pavement Density/ Jul. 1969/Prepared by Department of Highways State of Colorado—Planning and Research Division.

*Primary Examiner*—Diep N. Do
*Attorney, Agent, or Firm*—Schmeiser, Olsen & Watts

[57] ABSTRACT

The present invention relates generally to paving equipment. More particularly, the present invention relates to a paving material density indicator which has a selectively shaped sensor to control at least one of the depth, area, sensitivity and shape of a density determination. The effect on sensor capacitance is measured using a constant current source and is used to determine density of the paving material. The invention is also a method for determining density of paving material and a set of sensors for density determination.

11 Claims, 4 Drawing Sheets

PAVING MATERIAL DENSITY INDICATOR AND METHOD USING CAPACITANCE

BACKGROUND OF THE INVENTION

1. Technical Field

The present invention relates generally to paving equipment. More particularly, the present invention relates to a paving material density indicator and method for determining density of paving material by providing a sensor with a shape and size configured to have an electrical field with at least one of a controlled depth of penetration, controlled area, controlled shape, and controlled volume.

2. Related Art

During paving, paving material is usually laid at about 75% of acceptable compaction. However, during subsequent compaction it is highly advantageous to assure that the paving material is compacted to as close to total acceptable compaction as possible. Attaining total acceptable compaction assures the lack of variations in the material, such as air voids, that can create potential defects in the paving material. Unfortunately, the level of compaction is not readily apparent to the naked eye. In order to address this problem, measurement of dielectric properties of paving material is known to be very useful for determining material density, a key indicator of compaction level.

However, due to pavement laying machines used today becoming more adept at laying thinner pavement lifts, it has become necessary to have a reliable and convenient density determining device capable of measurement at differing depths, areas, shapes, and volumes of the pavement. Additionally, it has become necessary to have a density determining device which is faster than those available. Heretofore, no adequate paving material sensor capable of addressing the above problems has been devised. Accordingly, the present invention addresses a long felt need in the art.

One pavement density indicator device is that of Blackwell, U.S. Pat. No. 3,784,905. Blackwell's device measures dielectric properties of the asphalt which is representative o the change in density in the asphalt. The device of Blackwell has many disadvantages. For example, in order to obtain a reading, the Blackwell device must be moved at extremely slow speeds across the material being tested and, accordingly, requires an extended time period to provide a determination. The Blackwell device, due to its excessive weight, also requires a large sled frame (contact area) to be dragged across the pavement surface. Another disadvantage is limited adjustability of the depth of measurement of the device caused by the given set of electrodes only being able to vary the depth of measurement by changing the height of the electrodes.

In another apparatus, a nuclear source is used to determine density of pavement material. This device has a variety of obvious drawbacks. For instance, the device requires a licensed operator and a radiation shield (e.g., a lead enclosure). Furthermore, the device is non-adjustable for area and depth, time consuming in use, and heavy. The device is also very expensive.

Another disadvantage of the related art devices lies in their inability to adjust depth of measuring for variations in depth of pavement (e.g., when a new layer of pavement, called a lift, has been laid). When the related art devices are used to determine the density of a new layer of pavement, the measurement may go beyond the layer of new pavement and into the material below, hence, providing an inaccurate density indication. Similarly, the related art devices may not sense far enough into the new layer, e.g., where a dip has been filled, to assure a constant compaction level within the pavement lift.

Another disadvantage of the related art is their inability to vary the shape and area of the sensing area. Altering the shape and area of the sensor is advantageous for determining the density in particular pavement attributes, e.g., dips, joints odd shaped patches, etc.

Other devices, such as that of Harris, U.S. Pat. No. 3,400,331, incorporated herein by reference, have been used to detect the presence and dimensions of an object. However, Harris is incapable of detecting the density of the object. Furthermore, the Harris device requires that the sensor head remain as small as possible, a disadvantage to unlimited size and shape measurement.

SUMMARY OF THE INVENTION

It is a feature of this invention to overcome the above-listed disadvantages in the related art. Accordingly, the present invention is a paving material density sensor, the sensor having a shape and size configured to generate an electrical field with at least one of a controlled depth of penetration, controlled area, controlled shape, and controlled volume. The sensor subjects the material to an electrical field and the return signal obtained is used to measure the dielectric characteristics of the material as the latter effects the sensor capacitance. The effect on sensor capacitance is then used to determine density variations of the paving material. Since the depth, area, sensitivity, volume and shape of the determination can be changed, the present invention is more adjustable. As a result of the additional adjustability, the accuracy is increased relative to the related art devices.

Another advantage of the present invention is that it is very lightweight and can be carried by hand. A further advantage of the present invention is its ability to give instantaneous and accurate readings of variations in the material's density thereby reducing paving time since paving does not have to stop to provide a measurement. Furthermore, since the depth and area are selectable, a volume of the measured field is also adjustable. The sensor of the present invention is also configured to be in contact or non-contact with the pavement material during use and can correct the reading for varying standoff distances from the paving material. Another advantage of the present invention is that the sensor is provided as a guarded circuit for protecting measurements from stray capacitance.

The invention is also a set of density sensors as described above.

The invention is also a paving material density indicator having: a sensor having a shape and size to generate an electrical field with at least one of a controlled depth of penetration, controlled area, controlled shape, and controlled volume, and a circuit operatively coupled to the sensor to indicate the density of the paving material based on the effect on sensor capacitance caused by changes in the dielectric characteristics of the paving material. The circuit is preferably provided as a constant current source to provide a stable circuit and, hence, promote accuracy without being subject to the environmental characteristics that plague some of the related art.

Furthermore, the invention is a method for determining density of paving material including the steps of: 1) selecting a shape and size of a sensor to generate an electrical field having at least one of a controlled depth, controlled area, controlled shape and controlled volume; 2) generating the electrical field proximate the paving material; and 3) determining the density of the paving material from the effect on sensor capacitance due to the electrical field.

The foregoing and other features and advantages of the invention will be apparent from the following more particular description of preferred embodiments of the invention.

BRIEF DESCRIPTION OF THE DRAWINGS

The preferred embodiments of this invention will be described in detail, with reference to the following figures, wherein like designations denote like elements, and wherein.

DESCRIPTION OF THE PREFERRED EMBODIMENTS

While the preferred embodiments will be described in conjunction with the paving environment, one with ordinary skill in the art should understand that the material density indicator in accordance with the present invention may be applied in a variety of material density determining settings. For example, it is contemplated that the present invention may have applicability with soil or cement as well as paving material.

Figure 1:
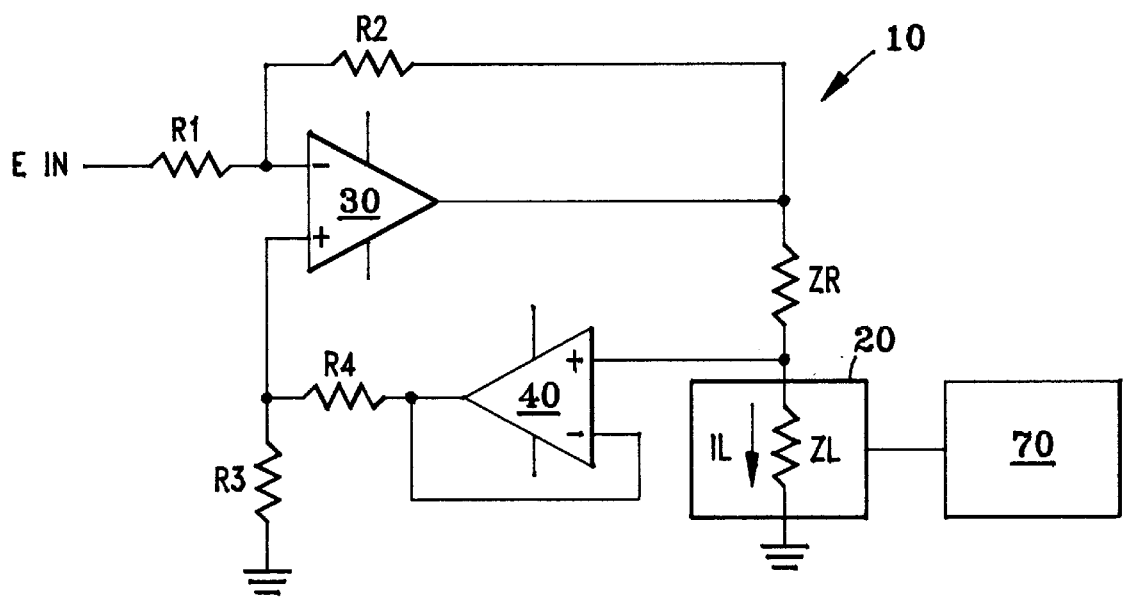
FIG. 1 shows a circuit diagram of the material density indicator in accordance with the present invention.

In FIG. 1, a circuit diagram in accordance with the present invention is shown. This circuit embodies a modified constant current source 10 which supplies an unvarying load current $I_L$. The circuit 10 includes an operational amplifier 30 with its inverting input connected to a resistance $R_1$ through which a reference voltage, $E_{IN}$, is provided. The inverting input of the amplifier 30 is also connected to a first end of a resistance $R_2$ which is in turn connected to the output of the amplifier 30 at its second end. The output of amplifier 30 and second end of the resistance $R_2$ are also connected to a first end of an impedance $Z_R$. The non-inverting input of the amplifier 30 is connected through a resistance $R_3$ to ground and to a first end of a feedback resistance $R_4$. The second end of the feedback resistance $R_4$ is connected to the output and inverting input of another operational amplifier 40, which acts as a unity gain amplifier in this setting. The non-inverting input of the amplifier 40 is connected to a second end of the impedance $Z_R$ and to sensor 20.

The sensor 20 is represented as a sensor/material impedance $Z_L$ which represents the combined impedance of the sensor structure and the material under test. The sensor 20, at its second end, is connected to ground. Furthermore, it is contemplated to provide a mechanism 70 for calibration of the sensor for particular paving materials. For instance, the mechanism 70 can be a microcomputer configured to output an actual density reading of the paving material based on an inputted reading from sensor 20. In this regard, a given shaped and sized sensor would be calibrated for a specific paving material and the paving material being used could be chosen on the computer, e.g. from a menu of paving materials.

In operation, the reference voltage $E_{IN}$ can take a variety of forms but is preferably in the range of 50 Hertz (Hz) to 50 kHz sine wave at 14V AC, most preferably at 2 kHz. The transfer function for the constant current source of FIG. 1 is as follows:

$$I_L/E_{IN} = -[R_2/(R_1 * Z_R)]$$

In operation, the impedance of the material $Z_L$ will be much greater than $R_2$ ($Z_L >> R_2$). Under these conditions, to maintain the load current constant, the load must be isolated from the feedback circuit. This is accomplished by the unity gain amplifier 40 between the feedback resistor $R_4$ and sensor 20. The circuit then operates as a constant current source as long as $E_{IN}$, $R_2$, $R_1$ and $Z_R$ are maintained constant and the sensor/material impedance $Z_L$ does not cause the circuit to exceed its voltage limits.

Figure 4:
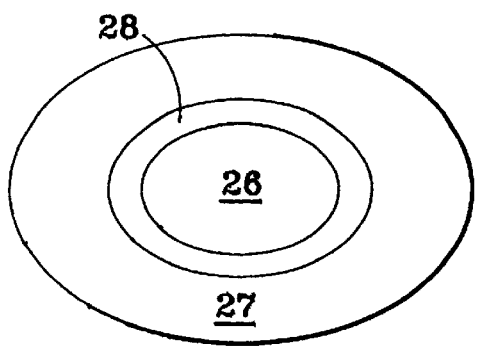
FIG. 4 shows a sensor in accordance with a first embodiment of the present invention.

FIG. 4 shows an exemplary structure of the sensor 20. The sensor 20 is in the form of a guarded circuit, i.e. guarded capacitor, including: an active inner element 26 surrounded by an intermediate guard element 28 which is surrounded by an outer element 27. Each of the elements is constructed of any conducting material, but is most preferably made of copper, aluminum or steel. The elements are held together and insulated from each other by a non-conductive material such as an epoxy. The provision of the sensor as a guarded capacitor promotes accuracy in that determinations are not subject to stray capacitance.

Figure 6:
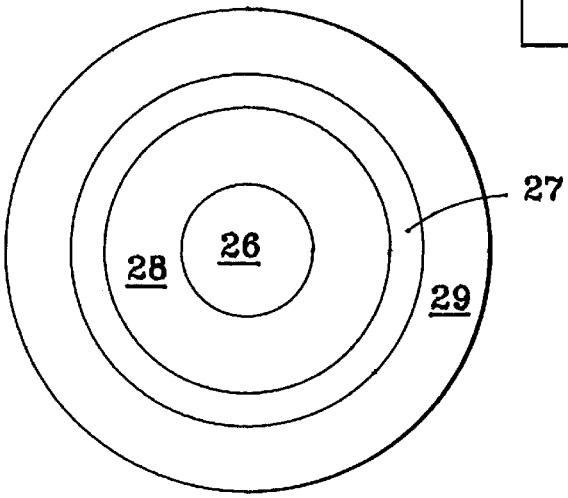
FIG. 6 shows a sensor in accordance with a third embodiment of the present invention.
Figure 8:
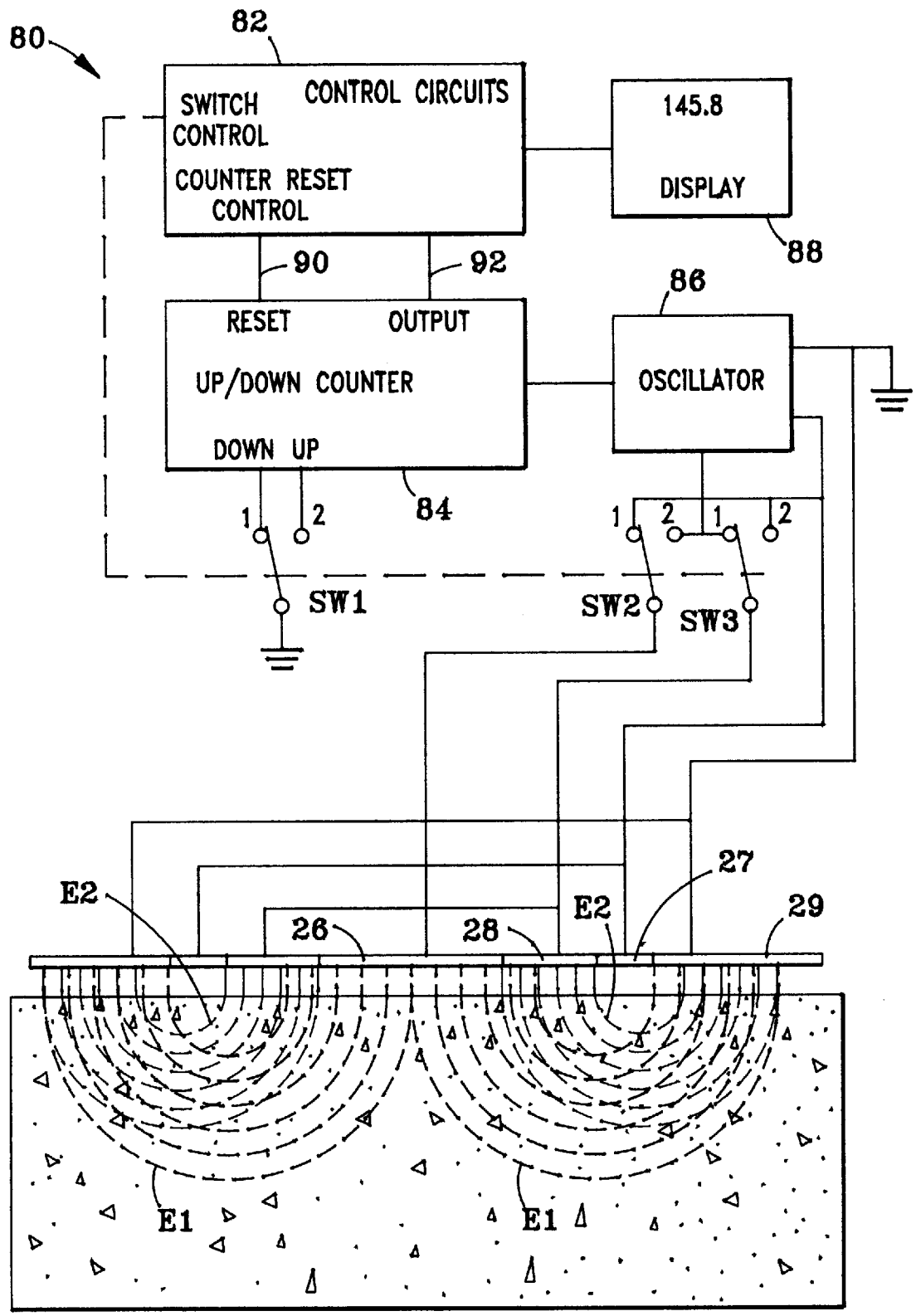
FIG. 8 shows a schematic view of a material density indicator in accordance with a fourth embodiment of the present invention.

Furthermore, if necessary, additional elements, e.g., element 29 as shown in FIGS. 6 and 8, surrounding those described above, and structured in similar fashion as those above, may be used to normalize the parameters of the device. For instance, additional elements are advantageous to make the electrical field more uniform or compensate for other parameters that may interfere with a measurement, e.g., moisture, temperature or the standoff distance from the material.

In terms of the standoff distance from the material, the capacitance caused by the air gap between the sensor and paving material can adversely affect the measurement if not rectified. To remedy this problem, an additional element 29 may be added to the sensor to attain a corrective signal proportional to the air gap. In order to acquire this corrective signal, as shown in FIG. 8, the present invention resonates an overall capacitance value from the additional element 29 with a known value of inductance and measures the resulting frequency. As an alternative, an RC oscillator, as will be described hereafter, may be used to acquire the resulting frequency. With either method, the resulting frequency is inversely proportional to the value of the air gap capacitance and, accordingly, can be used to correct the overall capacitance reading instantaneously with any change in the standoff distance.

There are a variety of ways to construct an RC oscillator that can attain the correction factor above. One such way is to arrange for a fixed voltage to be applied to the RC network that contains a fixed resistor and the effected capacitance.

This voltage is applied at a uniform repetition rate. When the voltage is applied, the capacitor will begin to charge. After a fixed time, the process is repeated. Since the charging rate is a function of the capacitance value, the resistor is fixed, this arrangement will produce a constant frequency, variable pulse width waveform or, in other words, a pulse width modulation. This type of waveform can be converted to a DC voltage that is proportional to the size of the gap by passing the waveform through a low pass filter.

Another arrangement with an RC network is to construct the circuit so that the RC combination determines the frequency of oscillation. Under these conditions, the frequency will be a function of the capacitance value if the resistor value is fixed. The frequency will be proportional to the size of the gap and can be used directly in a digital form or can be converted to a DC voltage by commonly used techniques.

Referring to FIG. 8, there is illustrated a variable frequency detector 80 for correcting for the standoff distance from the material. The variable frequency detector 80 includes a control circuit 82, an up/down counter 84, an oscillator 86, and a display 88.

In operation, the control circuit 82 resets the up/down counter 84 via a reset input 90, sets switches SW1, SW2, and SW3, to position 2, sets the up/down counter 84 to count up, and initiates counting. This produces an electric field E1 in the material. The frequency is counted for a predetermined time as determined by the control circuit 82.

When the predetermined time has elapsed, the control circuit 82 stops the count, sets switches SW1, SW2, and SW3, to position 1, sets the up/down counter 84 to count down, and initiates counting. This produces an electric field E2 in the material. Again, the frequency is counted for a predetermined time as determined by the control circuit 82.

Since the path length of E2 is shorter than E1, it has a higher capacitance and produces a lower frequency. This frequency is subtracted from the previous frequency value since the up/down counter 84 is now counting down.

When the predetermined time has elapsed, the control circuit 82 stops the count, transfers the difference between the two frequency values to the display 88 via output 92, and repeats the switching cycle. The difference between the two frequencies is proportional to the dielectric properties of the asphalt and can be related to the asphalt density.

Similarly to the above gap size correction, an additional element 29 can be added to make corrections for moisture. However, paving material moisture correction is more difficult to attain because the presence of moisture can manifest itself in many ways, e.g., as an energy dissipation factor or a change in dielectric constant. In order to attain a moisture correction, the present invention uses a sinusoidal source, such as the above described constant current source, to treat the moisture capacitance unknown as a complex impedance. The present invention then measures the resultant quadrature and in-phase components of the resultant waveform. The quadrature component is proportional to the dielectric of the paving material but, the in-phase component is a measure of the loss component or moisture content. Accordingly, the overall reading can be corrected for moisture content.

Figure 5:
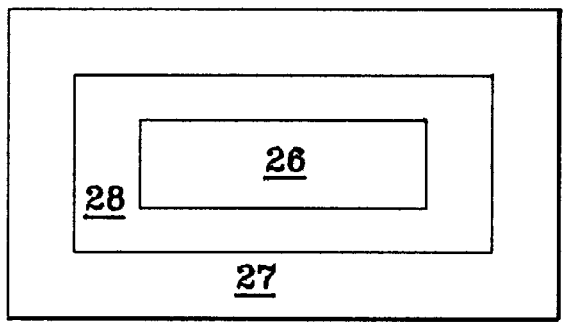
FIG. 5 shows a sensor in accordance with a second embodiment of the present invention.

Referring to FIGS. 4–6, illustrative shapes for the sensor are shown. FIG. 4 shows an elliptical shape; FIG. 5 shows a rectangular shape; and FIG. 6 shows a circular shape. Although, FIGS. 4–6 show the sensor 20 in three preferred shapes, the sensor can take a variety of alternative shapes. Furthermore, although the embodiments shown are fixed in nature, it is also envisioned to provide a sensor with an adjustable shape.

The adjustability of the shape and the size of the sensor 20 is a significant advantage to the present invention in that changing the shape and size of the sensor dictates the depth of penetration and area of the signal and, accordingly, the volume of the measurement field. Furthermore, changing the shape and size of the sensor 20 allows for a variation of the shape of the area tested and the sensitivity.

The capability to vary these features is important because a user can now adjust the determination to meet precise requirements and gain more accuracy. For instance, being able to accurately control the depth of penetration prevents imprecise determinations when the signal penetrates through a new lift coat into the underlying surface. Sensing of the underlying surface not only being unnecessary but also disruptive to an accurate density determinations of the new lift coat because the underlying surface may be more or less compacted by damage or vehicle travel over it. Similary, for example, when a user wishes to determine density at a joint between two new lift coats, he can now use, for instance, a long rectangular sensor to assure accurate sensing along the joint.

Figure 2:
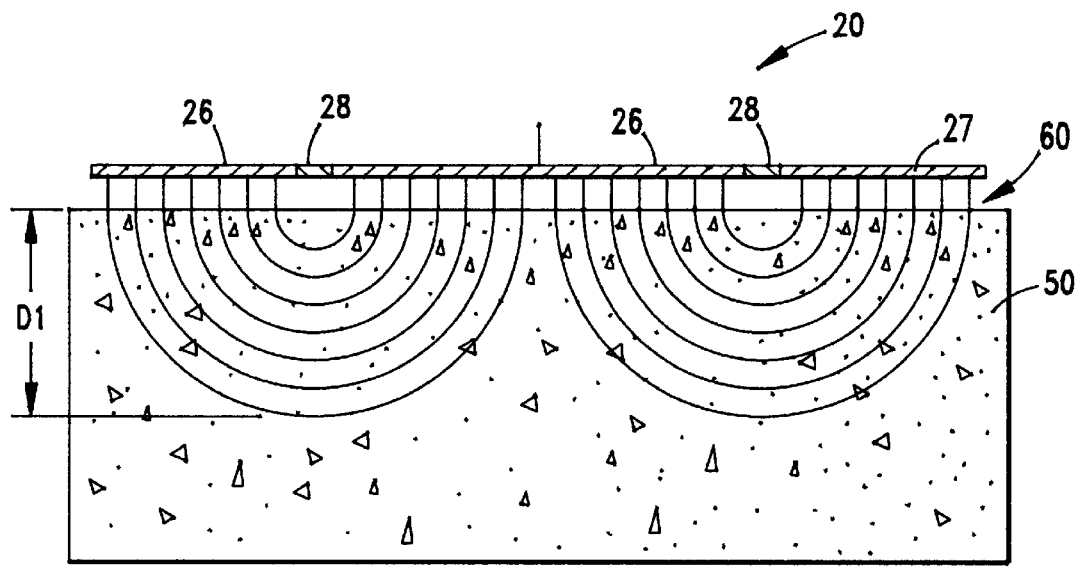
FIG. 2 shows a cross-sectional view of a material density indicator in accordance with a first embodiment of the present invention.
Figure 3:
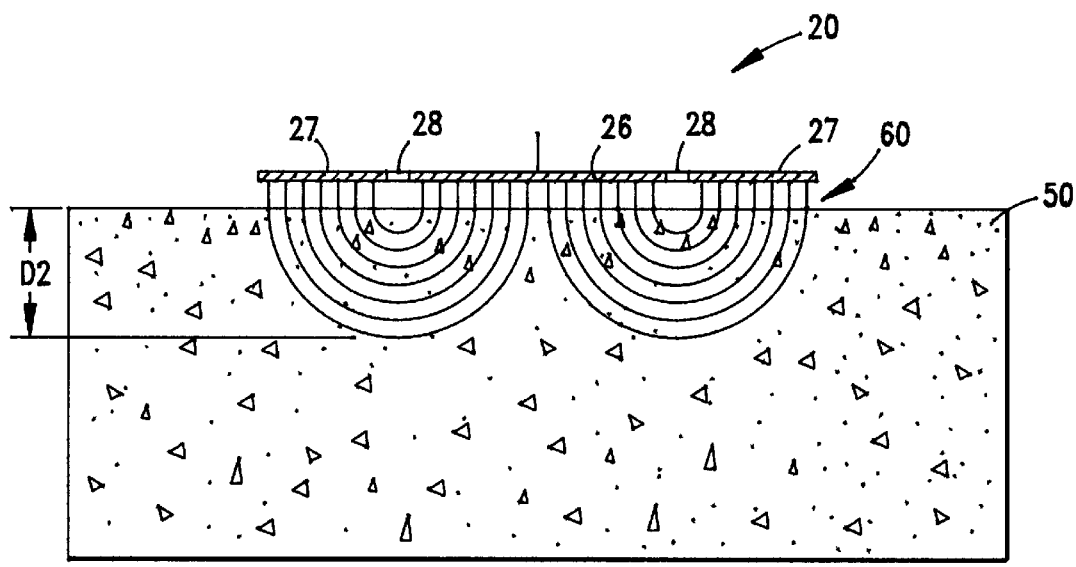
FIG. 3 shows a cross-sectional view of a material density indicator in accordance with a second embodiment of the present invention.
Figure 7:
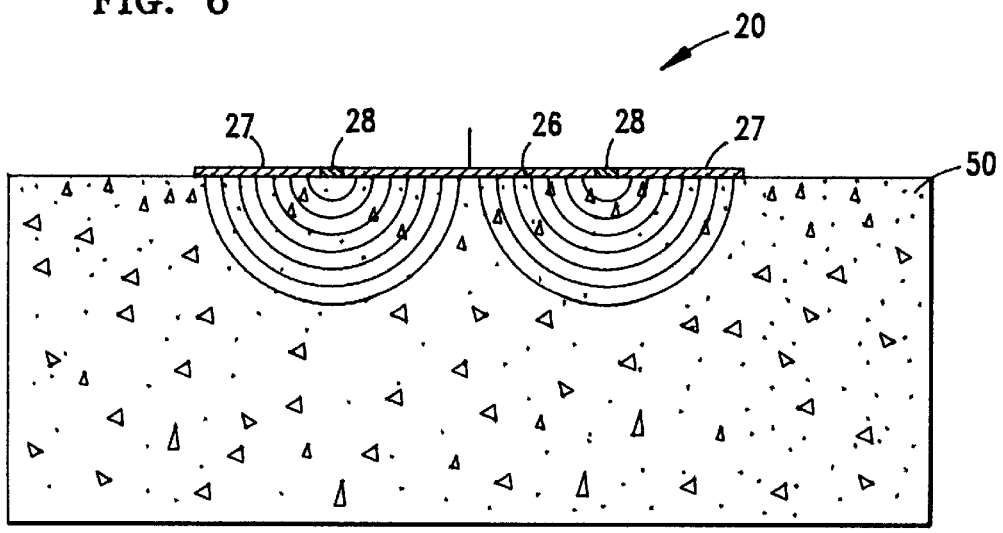
FIG. 7 shows a cross-sectional view of a material density indicator in accordance with a third embodiment of the present invention.

In operation, as shown in FIGS. 2, 3 and 7, the active element 26 emits an electrical signal into the paving material 50 to be used to determine the density of the paving material based on the effect on the sensor capacitance. The outer element 27 then receives this signal from the paving material, the signal having been altered by the dielectric characteristics of the material. During this time, the intermediate element 28 is at the same potential as the active element 26 but the current flowing therethrough is not the same as that flowing through the active element 26 ($I_L$).

The present invention is capable of determining paving material density in terms of: 1) variations in paving material density across a measurement area, and 2) actual density values. In order to determine the density of the paving material in terms of variations in density, the capacitive voltage in the constant current source 10 created by the dielectric characteristics of the paving material and detected by the sensor 20 is measured. Accordingly, variations in the voltage are used to determine density of the paving material in terms of density variations as the sensor passes over the paving material.

In order to determine the density in terms of actual density values of the paving material, e.g., 5 g/cm$^3$, a calibration of a given sensor at a given operational setting with regard to specific types of paving material at known compaction densities is provided. As a result, density measurements of the given sensor can be used to determine an actual density of a paving material in the field. As noted earlier, a mechanism 70 could be used to output the actual densities based on sensor input. Furthermore, a calibration of a set of sensors with a variety of shapes and sizes so that their respective depths of penetration, area and shape of measurement, and sensitivity can be pre-determined for a given type of paving material can be provided. Once one or both of the above-described calibrations has been conducted, sets of differently shaped and sized sensors can be packaged for use with given types of paving material, e.g., asphalt. Furthermore, the mechanism 70 may be adjusted to accommodate all of these various sensors.

In addition to the above density measurements, as explained earlier, the present invention can accommodate corrections of density measurement effecting parameters, e.g., standoff distance and moisture, through the use of additional elements 29 on the sensor.

FIG. 3 illustrates operation of a smaller sized sensor 20 which allows the depth of penetration to be reduced to D2 as opposed to the depth D1 shown in FIG. 2. Of note, as illustrated by comparing FIGS. 2 and 3 with FIG. 7, the sensor 20 can operate in contact with the paving material or out of contact with the paving material 50.

The provision of the constant current source enables the pavement density indicator to detect material density with accuracy. The constant current source also provides a stable system in that it is not alterable by environmental forces, e.g., electromagnetic interference or temperature. Accordingly, the potential for mismeasurement is reduced. Furthermore, the system in accordance with the present invention allows for instantaneous and continuous determinations which greatly reduces paving time.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention as defined in the following claims.

For example, it should be noted that the use of a constant current source is not the only way to determine the variations in sensor capacitance. Other alternative methods include: using fixed sinusoidal current and measuring voltage across the sensor; using fixed sinusoidal voltage and measuring current into the sensor; charging the sensor for a fixed time with a fixed current and measuring voltage; charging the sensor with a fixed current and measuring the time to reach a certain voltage; resonating the sensor with an inductor and determining frequency for a set resonant condition (e.g., ratio of sensor voltage to applied voltage); applying a fixed charge through a high impedance coupling and observing voltage output variation on sensor terminals; and applying a fixed charge and observing voltage output variations on sensor terminals. The selection of the method of capacitance measurement is dependent on, for example, capacitance level being measured, percentage of variation expected, resolution required, cable length, response desired (e.g., dynamic or static), sensor operative temperature, sensor configuration (e.g., single ended, half bridge, full bridge), and costs. Accordingly, other methods of measuring the capacitance are possible within the scope of the present invention.

We claim:

1. A paving material density indicator comprising:
    a sensor;
    a constant current source circuit operatively coupled to the sensor to generate an electric field from the sensor; and
    means for indicating the density of the paving material based on the effect on sensor impedance from the electrical field caused by changes in the dielectric characteristics of the paving materials.

2. The paving material density indicator of claim 1, wherein the circuit has a frequency in the range of 50 Hz to 50 kHz.

3. The paving material density indicator of claim 2, wherein the frequency is approximately 2 kHz.

4. The paving material density indicator of claim 1, wherein the constant current source circuit includes a unity gain amplifier.

5. The paving material density indicator of claim 1, wherein the sensor includes at least a first, second and third element, the elements being positioned one inside of another.

6. The paving material density indicator of claim 1, wherein the sensor has a shape selected from the group consisting of circular, elliptical, and polygonal.

7. The paving material density indicator of claim 1, wherein the paving material is one of asphalt and soil.

8. The paving material density indicator of claim 1, wherein the sensor is in contact or non-contact with the paving material during use.

9. The paving material density indicator of claim 1, further including a means for correcting for a distance of the sensor from the paving material and correcting the paving material density indication accordingly.

10. A method for determining density of paving material comprising the steps of:
    providing a set of calibrated density sensors, each sensor having at least one of a different shape and different size;
    selecting a sensor from the set of calibrated sensors;
    applying a constant current through the sensor to generate an electrical field proximate the paving material, the electric field having a depth, area, shape and volume determined by the selected sensor; and
    determining the density of the paving material from the effect on sensor impedance due to changes in the electrical field.

11. A method for determining density of paving material comprising the steps of:
    providing a sensor;
    generating a first electrical field from the sensor proximate the paving material;
    generating a second electrical field having a path length different than the first electrical field from the sensor proximate the paving material; and
    determining the density of the paving material, including correcting for a standoff distance of the sensor from the paving material, using the difference in frequency between the first and second electrical fields.

* * * * *